US012714845B2

(12) United States Patent
Ryan et al.

(10) Patent No.: US 12,714,845 B2
(45) Date of Patent: Aug. 25, 2026

(54) CATHETER BLOOD PUMP DISTAL BEARING ASSEMBLIES

(71) Applicant: SUPIRA MEDICAL, INC., Los Gatos, CA (US)

(72) Inventors: Ari Ryan, Sunnyvale, CA (US); Shayan Assani, Sunnyvale, CA (US); Daniel Varghai, Scotts Valley, CA (US); Crissly Crisostomo, Campbell, CA (US)

(73) Assignee: SUPIRA MEDICAL., INC., Los Gatos, CA (US)

( * ) Notice: Subject to any disclaimer, the term of this patent is extended or adjusted under 35 U.S.C. 154(b) by 204 days.

(21) Appl. No.: 18/554,746

(22) PCT Filed: Apr. 6, 2022

(86) PCT No.: PCT/US2022/023634
§ 371 (c)(1),
(2) Date: Oct. 10, 2023

(87) PCT Pub. No.: WO2022/216799
PCT Pub. Date: Oct. 13, 2022

(65) Prior Publication Data

US 2024/0181238 A1 Jun. 6, 2024

Related U.S. Application Data

(60) Provisional application No. 63/171,721, filed on Apr. 7, 2021.

(51) Int. Cl.
*A61M 60/13* (2021.01)
*A61M 60/216* (2021.01)
*A61M 60/414* (2021.01)
*A61M 60/818* (2021.01)
*A61M 60/857* (2021.01)

(52) U.S. Cl.
CPC .......... *A61M 60/13* (2021.01); *A61M 60/216* (2021.01); *A61M 60/414* (2021.01); *A61M 60/818* (2021.01); *A61M 60/857* (2021.01)

(58) Field of Classification Search
None
See application file for complete search history.

(56) References Cited

U.S. PATENT DOCUMENTS 4,625,712 A 12/1986 Wampler
4,753,221 A 6/1988 Kensey et al.
5,061,256 A 10/1991 Wampler
5,287,858 A 2/1994 Hammerslag et al.
5,507,629 A 4/1996 Jarvik
(Continued)

FOREIGN PATENT DOCUMENTS

CA 3014105 A1 8/2017
EP 3131599 A1 2/2017
(Continued)

*Primary Examiner* — Mallika D Fairchild
(74) *Attorney, Agent, or Firm* — Shay Glenn LLP

(57) ABSTRACT

Catheter blood pumps that include an expandable pump portion. The pump portions include a collapsible blood conduit that defines a blood lumen. The collapsible blood conduits include a collapsible scaffold adapted to provide radial support to the blood conduit. The pump portion also includes one or more impellers.

19 Claims, 6 Drawing Sheets

(56) References Cited

U.S. PATENT DOCUMENTS 5,735,892 A 4/1998 Myers et al.
5,827,171 A 10/1998 Dobak, III et al.
6,007,478 A 12/1999 Siess et al.
6,053,943 A 4/2000 Edwin et al.
6,685,696 B2 2/2004 Fleischhacker et al.
6,712,844 B2 3/2004 Pacetti
7,022,100 B1 4/2006 Hosn et al.
7,027,875 B2 4/2006 Siess et al.
7,220,275 B2 5/2007 Davidson et al.
7,828,710 B2 11/2010 Shifflette
8,388,565 B2 3/2013 Shifflette
8,485,961 B2 7/2013 Campbell et al.
8,535,211 B2 9/2013 Campbell et al.
8,591,393 B2 11/2013 Walters et al.
8,597,170 B2 12/2013 Walters et al.
8,721,517 B2 5/2014 Zeng et al.
8,734,508 B2 5/2014 Hastings et al.
8,814,776 B2 8/2014 Hastie et al.
8,814,933 B2 8/2014 Siess
8,849,398 B2 9/2014 Evans
8,932,141 B2 1/2015 Liebing
8,934,956 B2 1/2015 Glenn et al.
9,028,216 B2 5/2015 Schumacher et al.
9,028,392 B2 5/2015 Shifflette
9,072,825 B2 7/2015 Pfeffer et al.
9,138,518 B2 9/2015 Campbell et al.
9,180,235 B2 11/2015 Forsell
9,446,179 B2 9/2016 Keenan et al.
9,512,839 B2 12/2016 Liebing
9,833,550 B2 12/2017 Siess
9,872,948 B2 1/2018 Siess
10,052,419 B2 8/2018 Er
10,208,763 B2 2/2019 Schumacher et al.
10,357,598 B2 7/2019 Aboul-Hosn et al.
10,525,178 B2 1/2020 Zeng
10,881,770 B2 1/2021 Tuval et al.
10,894,115 B2 1/2021 Pfeffer et al.
11,123,538 B2 9/2021 Epple et al.
11,185,677 B2 11/2021 Salahieh et al.
11,268,521 B2 3/2022 Toellner
11,280,345 B2 3/2022 Bredenbreuker et al.
11,511,103 B2 11/2022 Salahieh et al.
11,850,413 B2 12/2023 Zeng et al.
12,017,056 B2 6/2024 Guo et al.
2005/0277803 A1 12/2005 Pecor
2007/0250148 A1 10/2007 Perry et al.
2014/0148638 A1 5/2014 LaRose et al.
2015/0238671 A1 8/2015 Mesallum
2015/0328382 A1 11/2015 Corbett et al.
2016/0022890 A1 1/2016 Schwammenthal et al.
2016/0053763 A1 2/2016 Toellner
2017/0014562 A1 1/2017 Liebing
2017/0037860 A1 2/2017 Toellner
2017/0100527 A1 4/2017 Schwammenthal et al.
2017/0173242 A1 6/2017 Anderson et al.
2017/0232169 A1 8/2017 Muller
2017/0340788 A1 11/2017 Korakianitis et al.
2018/0080326 A1 3/2018 Schumacher et al.
2018/0149164 A1 5/2018 Siess
2018/0303990 A1 10/2018 Siess et al.
2019/0175805 A1* 6/2019 Tuval .................... A61M 60/81
2019/0328948 A1* 10/2019 Salahieh ............. A61M 60/414
2020/0121835 A1 4/2020 Farago et al.
2020/0237981 A1 7/2020 Tuval et al.
2020/0316268 A1 10/2020 Antoni et al.
2022/0203084 A1 6/2022 Zarins et al.

FOREIGN PATENT DOCUMENTS

EP 3153190 A1 4/2017
EP 3000493 B1 5/2017
WO WO01/019444 A1 3/2001
WO WO2015/177793 A2 11/2015
WO WO2018/061002 A1 4/2018
WO WO2018/067410 A1 4/2018
WO WO2018/078615 A1 5/2018
WO WO2018/088939 A1 5/2018
WO WO2018/096531 A1 5/2018
WO WO2019/191851 A1 9/2019
WO WO2019/194956 A1 10/2019
WO WO-2021026472 A1 * 2/2021 .......... A61M 60/825

* cited by examiner

CATHETER BLOOD PUMP DISTAL BEARING ASSEMBLIES

CROSS REFERENCE TO RELATED APPLICATIONS

This application claims the benefit of U.S. Application No. 63/171,721, filed Apr. 7, 2021, titled "CATHETER BLOOD PUMP DISTAL BEARING ASSEMBLIES" which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in combination with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

The disclosure is related to intravascular blood pumps and their methods of and manufacture.

A catheter blood pump (e.g., 10, 100) is provided, comprising a collapsible and expandable blood conduit (e.g., 12, 120) having an inflow portion, proximal and distal impellers (e.g., 14, 140) at least partially disposed in the blood conduit, a rotatable drive assembly (e.g., 60, 600) coupled to and extending through the proximal impeller, through the distal impeller, through a distal bearing assembly (e.g., 20, 200) that is proximate the inflow portion, and extending distally beyond the distal bearing assembly, a plurality of distal struts (e.g., 16) coupled to the blood conduit and extending distally from the blood conduit at the inflow portion, the plurality of distal struts coupled to the distal bearing assembly, and a force applier (e.g., 30) secured to the distal bearing assembly and to a distal end of the rotatable drive mechanism, and extending therebetween, wherein distal ends of the plurality of distal struts, the distal bearing assembly, and a proximal end (e.g., 36) of the force applier are axially movable relative to the rotatable drive assembly to facilitate collapse and expansion of the blood conduit.

In some embodiments, the force applier is adapted to apply a proximally directed force on the distal bearing housing when the blood conduit is in an expanded configuration.

In one example, the proximally directed force is not large enough to prevent distal movement of the distal bearing assembly in response to sheathing forces, and thereby facilitates collapse of the blood conduit during sheathing.

In some embodiments, the force applier comprises a compressed spring.

In additional examples, the force applier applies a distally directed force to a drive cable extension (e.g., 70, 700) to thereby maintain tension in a drive cable in a region between the distal and proximal impeller to prevent whipping therein when the pump is operated.

In some implementations, maintaining tension prevents compression of the drive cable in the region between the impellers.

In additional examples, the force applier applies a compressive load to the distal bearing assembly sufficient to maintain axial contact between at least two axially adjacent bearings disposed in the distal bearing assembly.

In some embodiments, the force applier translates rotational force from a distal end of a drive cable (and optionally from a drive cable extension such as 70 or 700) to a bearing housing structure (e.g., 21, 210) in the distal bearing assembly.

In some embodiments, the pump further comprises a sleeve secured to the distal bearing assembly and disposed about the force applier, the sleeve extending further distally than the force applier.

In some examples, the sleeve has a flexible distal end, and wherein the sleeve flexible end has a bend limiter that prevents the flexible end from contacting the force applier.

In other embodiments, the bend limiter comprises a size of at least one gap formed through the sleeve.

In one embodiment, the sleeve has a proximal end that is less flexible (optionally a solid tube) than a region distal to the proximal end.

In other embodiments, the sleeve comprises a hypotube.

A catheter blood pump is provided, comprising a collapsible and expandable blood conduit, proximal and distal impellers at least partially disposed in the blood conduit, a rotatable drive assembly coupled to and extending through the proximal impeller, through the distal impeller, through a distal bearing assembly that is proximate the inflow, and extending distally beyond the distal bearing assembly, a plurality of distal struts coupled to the blood conduit and extending distally from the blood conduit at a pump inflow, the plurality of distal struts coupled to the distal bearing assembly, and a spring (optionally compressed) secured to the distal bearing assembly and to a distal end of the rotatable drive assembly (optionally to a drive cable extension, such as 70, 700), and extending therebetween, wherein distal ends of the plurality of distal struts, the distal bearing assembly, and a proximal end of the force applier are axially movable relative to the rotatable drive assembly to facilitate collapse and expansion of the blood conduit.

A catheter blood pump is additionally provided, comprising a collapsible and expandable blood conduit, proximal and distal impellers at least partially disposed in the blood conduit, a rotatable drive assembly coupled to and extending through the proximal impeller, through the distal impeller, through a distal bearing assembly that is proximate the inflow, and extending distally beyond the distal bearing assembly, a plurality of distal struts coupled to the blood conduit and extending distally from the blood conduit at a pump inflow, the plurality of distal struts coupled to the distal bearing assembly, and a sleeve coupled to the distal bearing assembly and extending about the rotatable drive assembly and distally thereof, the sleeve having a variable flexibility along its length with greater flexibility in a distal region than in a proximal region where it is coupled to the distal bearing assembly, wherein the flexibility is such that the sleeve distal end can bend but is prevented from contacting the rotatable drive assembly therein.

In some embodiments, the rotatable drive assembly comprises a distal extension (e.g., 70, 700) coupled to a distal end of a drive cable.

In other embodiments, distal ends of the plurality of distal struts, the distal bearing assembly, and a proximal end of the force applier are axially movable relative to the rotatable drive assembly to facilitate collapse and expansion of the blood conduit.

A catheter blood pump is provided, comprising a collapsible and expandable blood conduit, proximal and distal impellers at least partially disposed in the blood conduit, a rotatable drive assembly coupled to and extending through the proximal impeller, through the distal impeller, through a distal bearing assembly that is proximate the inflow, and extending distally beyond the distal bearing assembly, a plurality of distal struts coupled to the blood conduit and extending distally from the blood conduit at a pump inflow, the plurality of distal struts coupled to the distal bearing assembly, and wherein distal ends of the plurality of distal struts, the distal bearing assembly, and a proximal end of the force applier are axially movable relative to the rotatable drive assembly to facilitate collapse and expansion of the blood conduit, and wherein when the blood conduit is in an expanded configuration, a proximally directed force is being applied to a distal end of the distal bearing assembly.

In some embodiments, a force applier (optionally a compressed spring) applies the proximally directed load.

A catheter blood pump is further provided, comprising a collapsible and expandable blood conduit, proximal and distal impellers at least partially disposed in the blood conduit, a rotatable drive assembly coupled to and extending through the proximal impeller, through the distal impeller, through a distal bearing assembly that is proximate the inflow, and extending distally beyond the distal bearing assembly, a plurality of distal struts coupled to the blood conduit and extending distally from the blood conduit at a pump inflow, the plurality of distal struts coupled to the distal bearing assembly, and wherein distal ends of the plurality of distal struts, the distal bearing assembly, and a proximal end of the force applier are axially movable relative to the rotatable drive assembly to facilitate collapse and expansion of the blood conduit, and wherein when the blood conduit is in an expanded configuration, a distally directed force is being applied to a drive cable extension (e.g., 70, 700), the drive cable extension coupled (directly or indirectly) to a distal end of the drive cable.

In some embodiments, the drive cable extension has an internal channel (e.g., 71) with a distal region, the internal channel configured to facilitate guidewire passage from a tip (e.g., 50) internal lumen and into the extension (e.g., 70).

A catheter blood pump is further provided, comprising a collapsible and expandable blood conduit having an outflow portion, a proximal impeller at least partially disposed in the blood conduit, a rotatable drive assembly coupled to and extending through a proximal bearing assembly that is proximate to the outflow portion, through the proximal impeller, a plurality of proximal struts coupled to the blood conduit and extending proximally from the blood conduit at the outflow portion, the plurality of distal struts coupled to the proximal bearing assembly, and a force applier secured to the proximal bearing assembly and to the rotatable drive mechanism, and extending therebetween, wherein proximal ends of the plurality of proximal struts, the proximal bearing assembly, and a proximal end of the force applier are axially movable relative to the rotatable drive assembly to facilitate collapse and expansion of the blood conduit.

In some embodiments, the force applier is adapted to apply a distally directed force on the proximal bearing housing when the blood conduit is in an expanded configuration.

In other embodiments, the distally directed force is not large enough to prevent proximal movement of the distal bearing assembly in response to sheathing forces, and thereby facilitates collapse of the blood conduit during sheathing.

In one example, the force applier comprises a compressed spring.

In additional embodiments, the force applier applies a compressive load to the proximal bearing assembly sufficient to maintain axial contact between at least two axially adjacent bearings disposed in the proximal bearing assembly.

In one embodiment, the pump further comprises a sleeve secured to the proximal bearing assembly and disposed about the force applier, the sleeve extending further proximally than the force applier.

In some examples, the sleeve has a flexible proximal end, and wherein the sleeve flexible proximal end has a bend limiter that prevents the flexible end from contacting the force applier.

In another embodiment, the bend limiter comprises a size of at least one gap formed through the sleeve.

DETAILED DESCRIPTION

Some intravascular blood pumps may include a pump portion that is collapsible and expandable, examples of which are described in the Appendix herein and in the disclosures of the following PCT publications: WO2018/226991, WO2019/094963, WO2019/152875, WO2020 028537, and WO 2020/073047, the disclosures of which are incorporated by reference herein for all purposes. The collapsible pump portion may include a collapsible blood conduit and one or more collapsible impellers therein, and a drive cable coupled to the one or more impellers such that rotation of the drive cable (e.g., via an external motor) causes the rotation of the one or more impellers.

Depending on the configuration of the collapsible pump portion, it may be necessary or at least beneficial for one or both ends of the collapsible pump portion to be able to move axially when the pump is sheathed for delivery and/or removal from the patient. Pump portions herein may include a proximal impeller and/or a distal impeller, with the proximal impeller closer to a pump outflow and the distal impeller closer to pump inflow. A drive assembly, which may include a drive cable and/or drive shaft (which may be used interchangeably herein), may be coupled to and pass through one or both impellers, and may also extend distally beyond the distal impeller (or distally beyond the proximal impeller if no distal impeller is provided). In examples herein (such as FIGS. 1A-1D and 2A-2B), the drive mechanism also extends into, through, and distally beyond bearing assembly of the distal most impeller. Collapsible pump portions may include a plurality of struts at the inflow and outflow, ends of which may be coupled to generally non-expandable parts of the catheter, while other ends of the struts are coupled to the collapsible and expandable blood conduit and are generally adapted to expand when the pump is unsheathed. While embodiments herein may be described with respect to a distal portion of the pump portion, such as the region around the distal impeller, it should be understood that these embodiments can also be applied to the proximal portion, including the proximal impeller.

Some pump portions herein (e.g., in FIGS. 1A-2B) include a drive cable that is coupled to a distal impeller (optionally to an impeller shaft to which the impeller is coupled), wherein the pump also includes a distal bearing assembly that is coupled to a plurality of inflow struts. The distal bearing assembly may be axially movable relative to the rotatable drive cable, which may facilitate or case the collapse of the distal end of the collapsible pump during sheathing. In these examples (e.g., in FIGS. 1A-2B), the distal bearing assembly is axially movable relative to a drive cable that extends through the distal bearing assembly and distally beyond the distal bearing assembly, as shown in FIGS. 1A-2D.

Figure 1A:
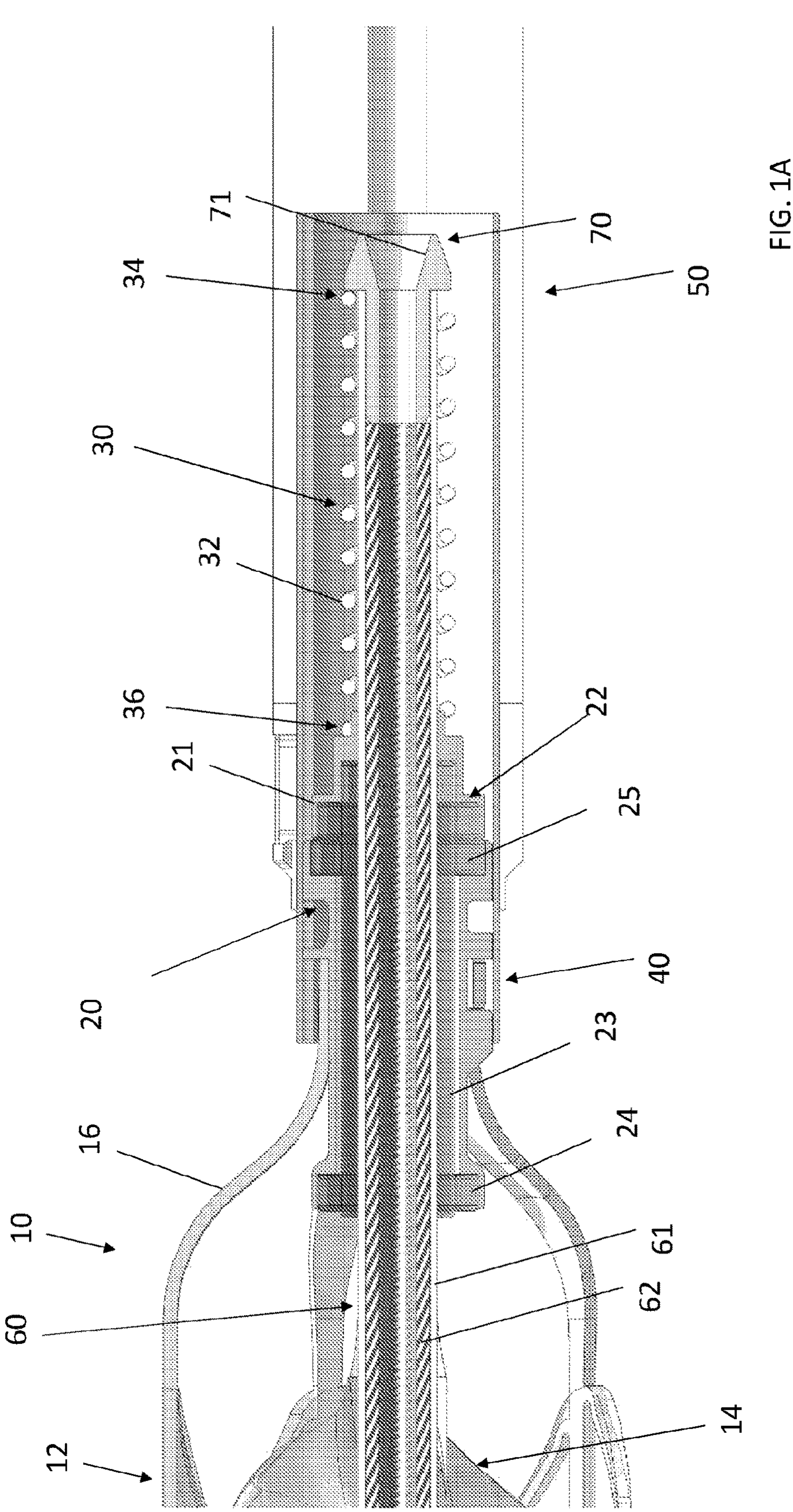
FIGS. 1A-1D illustrate one embodiment of a blood pump that includes collapsible and expandable blood conduit with a bearing assembly and pump portion that are axially moveable relative to an inner drive assembly.
Figure 1B:
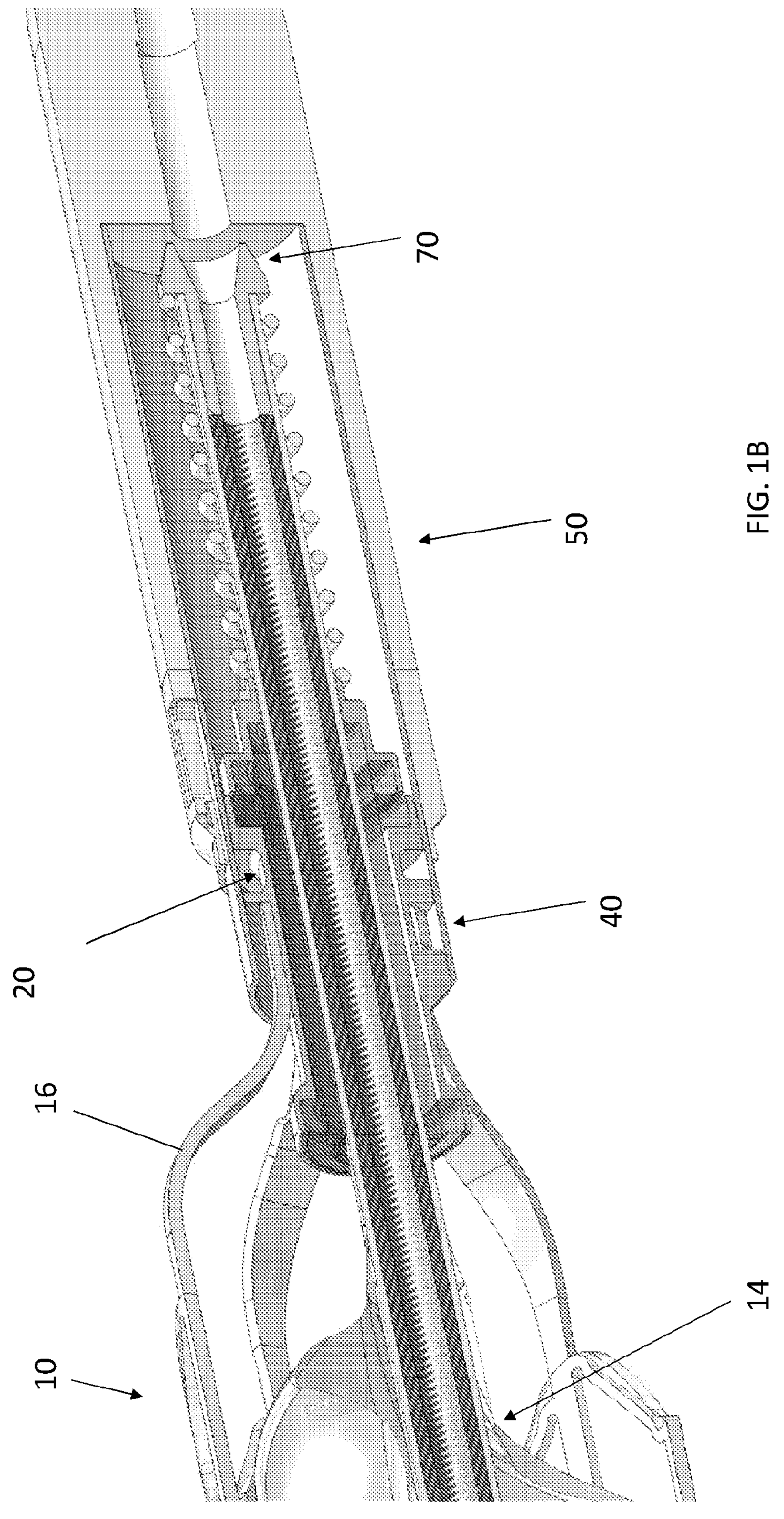
Figure 1C:
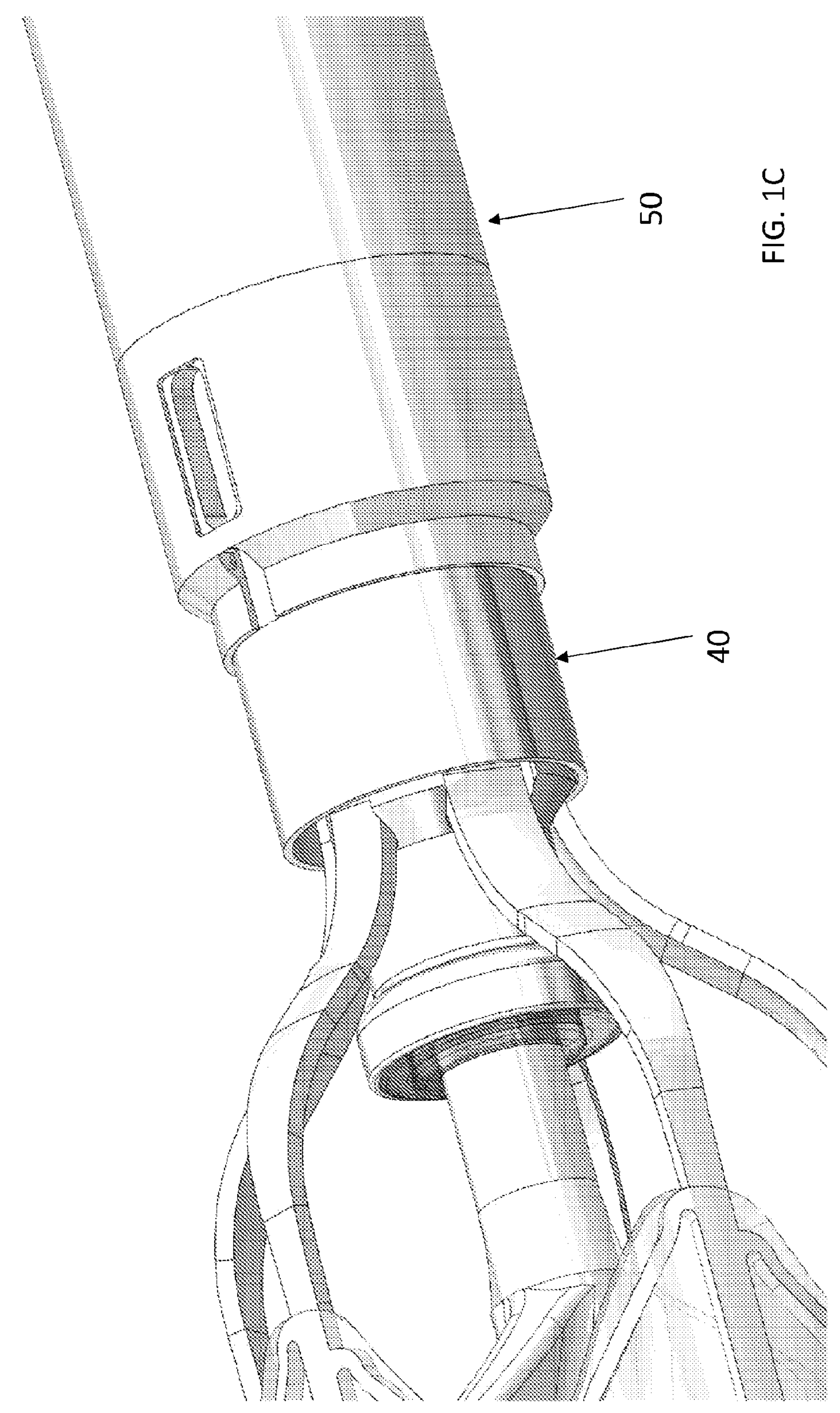
Figure 1D:
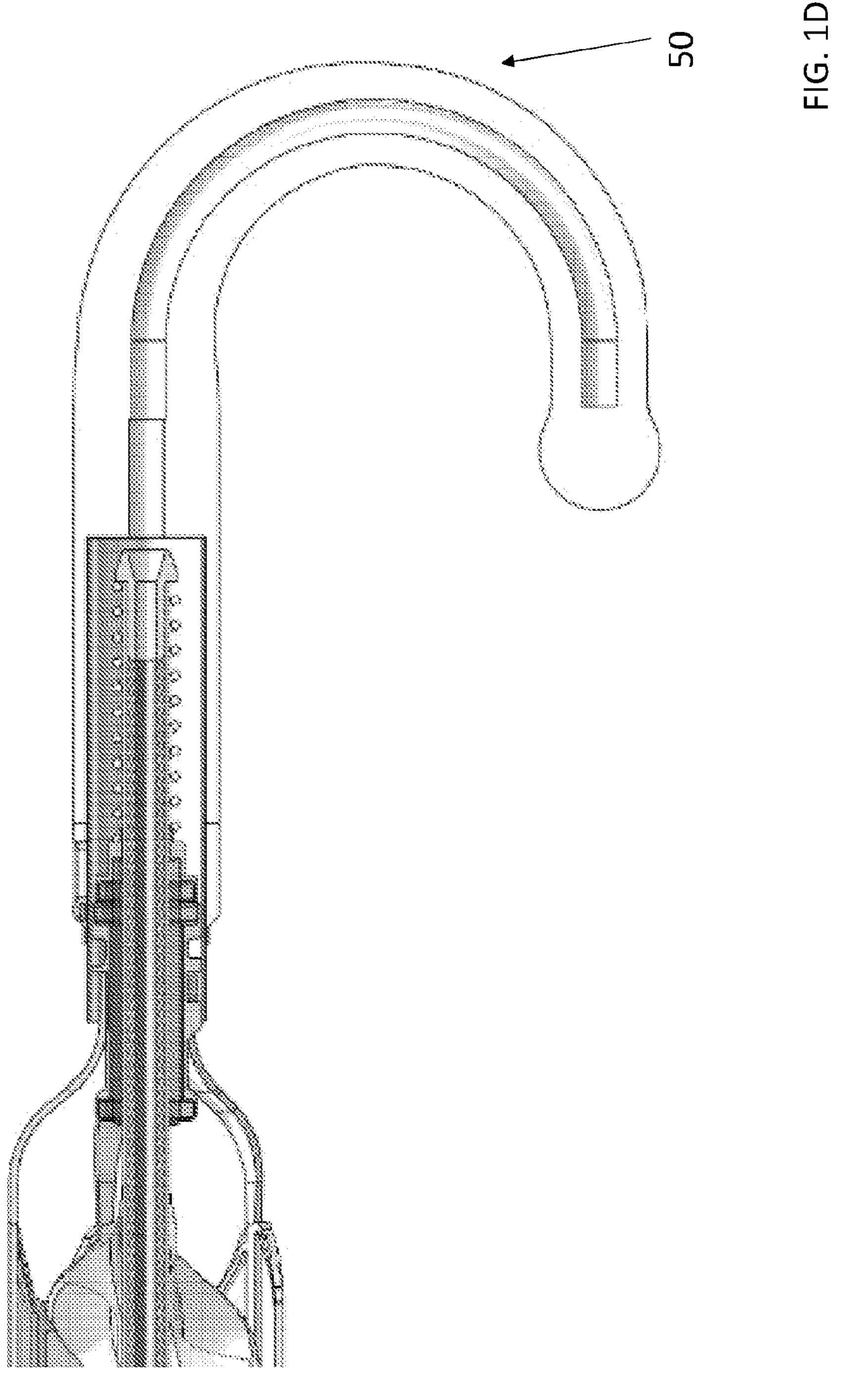
Figure 2A:
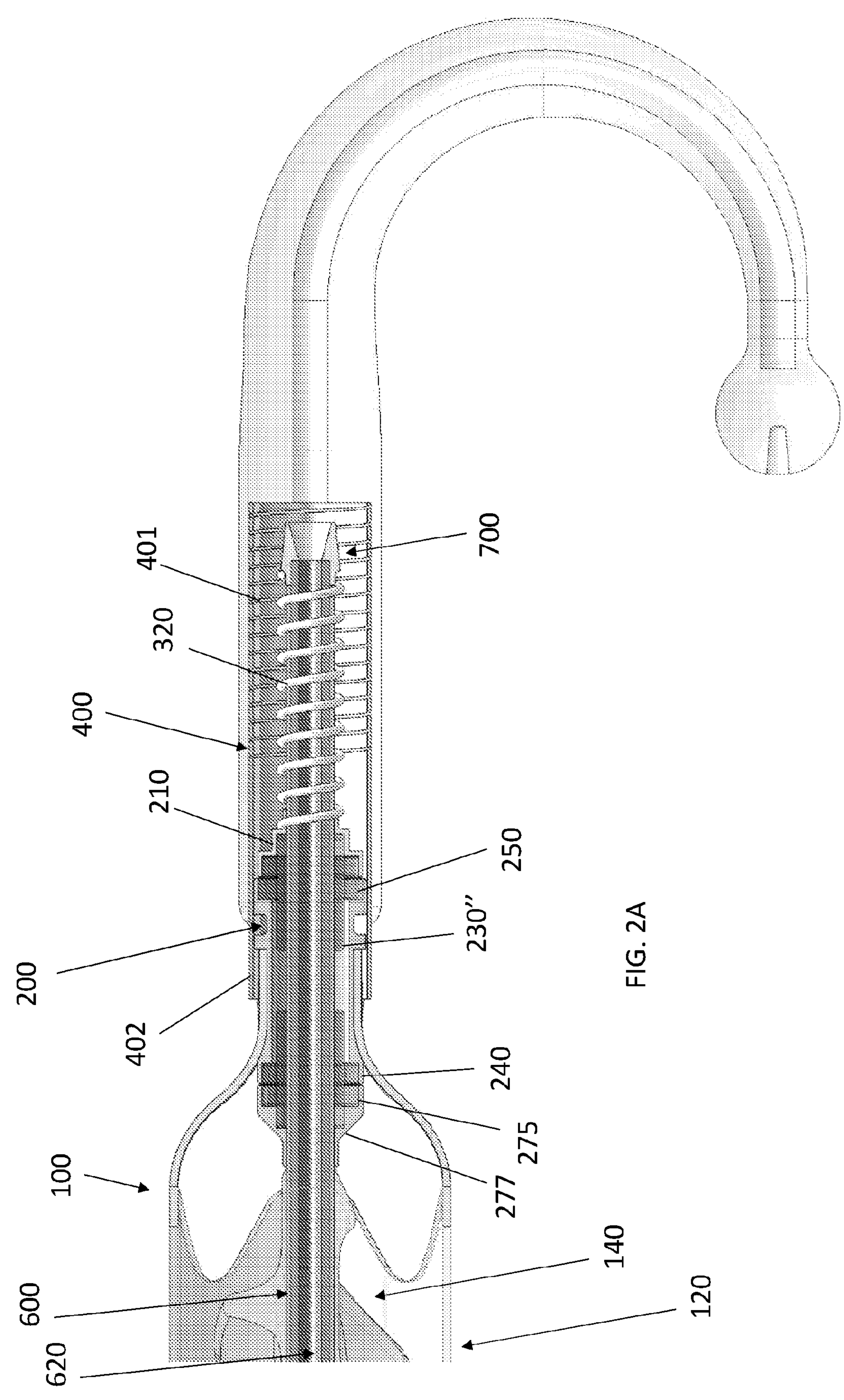
FIGS. 2A-2B illustrate another embodiment of a blood pump that includes collapsible and expandable blood conduit with a bearing assembly and pump portion that are axially moveable relative to an inner drive assembly.
Figure 2B:
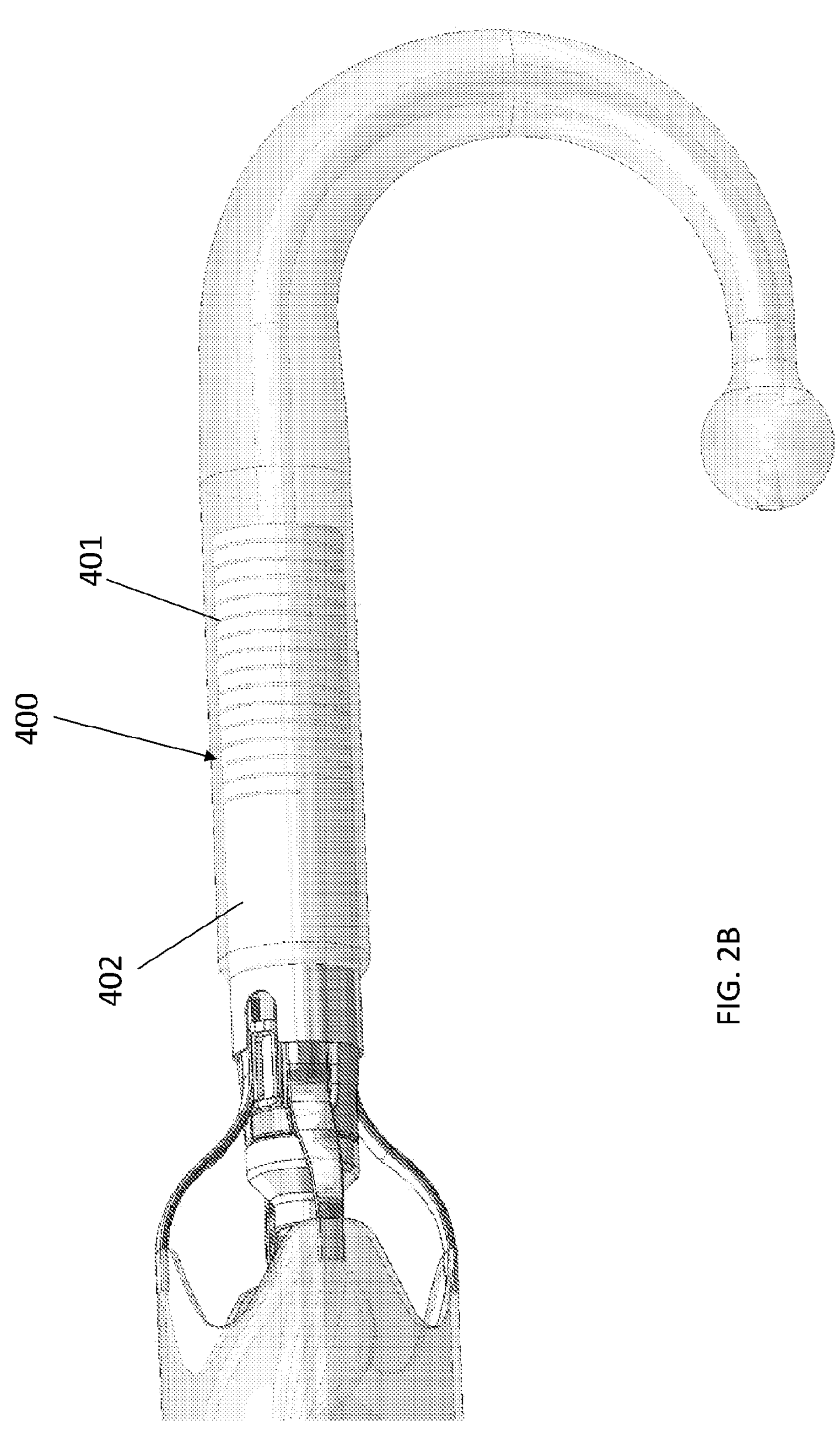

FIGS. 1A-1D illustrate a distal region of an exemplary pump portion with a distal bearing assembly and pump distal end that are axially moveable relative to an inner drive assembly, which facilitates collapsing (sheathing) and expansion (unsheathing) of the pump portion. FIGS. 2A and 2B illustrate another example of a pump portion with a distal bearing assembly and pump distal end that are axially moveable relative to an inner drive assembly, which facilitates collapsing (sheathing) and expansion (unsheathing) of the pump portion.

It may be generally beneficial to allow for axial motion between the distal bearing assembly and the drive cable passing therethrough, while at the same time providing some amount of control or limit on that relative motion. It may also be beneficial to apply a force to the distal bearing assembly and/or distal end of the rotatable drive assembly during operation of the pump. Any of the springs herein that are adapted to provide any of the one or more exemplary functions herein may be considered a particular implementation of one or more of a force applier, a distal bearing position controller, limiter or influencer, a distal bearing movement controller, limiter or influencer, and/or a force absorber. Any of the springs herein may be strong under tension and weak under compression.

The force appliers herein (e.g., springs) herein may be adapted to provide one or more of any of the exemplary non-limiting functions herein, and the functions provided by the spring may depend on the construction of the remainder of the pump portion.

FIGS. 1A-1D illustrate an exemplary pump portion 10 that includes a distal bearing assembly 20 that is adapted and constructed to move or slide axially (distally and/or proximally) relative to a rotatable drive assembly 60 therein that is coupled to one or more impellers (such as distal impeller 14 or a proximal impeller (not shown)). The pump portion may also include a proximal impeller and a proximal bearing housing that is at or near the pump outflow (not shown). The distal bearing assembly 20 can move distally relative to the drive assembly 60 when the pump is sheathed and collapsed, and the distal bearing assembly can move proximally relative to the drive assembly 60 when the pump is unsheathed and expands. The axial movement of the distal bearing assembly and the distal end of struts 16 may be referred to herein as a slidable arrangement.

It should be understood that in some embodiments, the blood pump may include only a proximal impeller. In these embodiments, the blood pump can include a proximal bearing assembly that is adapted and constructed to move or slide axially (distally and/or proximally) relative to a rotatable drive assembly therein that is coupled to the proximal impeller. The proximal bearing assembly can move distally relative to the drive assembly when the pump is sheathed and collapsed, and the distal bearing assembly can move proximally relative to the drive assembly when the pump is unsheathed and expands. The axial movement of the proximal bearing assembly and the proximal end of struts may also be referred to herein as a slidable arrangement.

In this example, the catheter blood pump also includes a force applier 30 that in this embodiment comprises spring 32. Spring 32 has a distal end 34 and proximal end 36. Distal end 34 of spring 32 is coupled to drive cable extension 70 (which rotates) and proximal end 36 of spring 32 is coupled to housing 21, which may be a thrust bearing housing and is considered part of the distal bearing assembly 20. Drive cable extension 70 is coupled to an inner surface of the distal end of impeller shaft 61 as shown. Impeller shaft 61 is coupled to distal impeller 14 and to drive cable 62. Extension 70 may also be coupled to the distal end of drive cable 62. Rotation of drive cable 62 and impeller shaft 61 causes the rotation of extension 70, which causes the rotation of spring 32, housing 21, and bearing 22 therein, which may be a thrust bearing. Elongate bearing 23 also rotates, and which is shown extending from the proximal end of distal bearing assembly 20 to the distal end region of distal bearing assembly 20. In this example bearings 24 and 25 do not rotate, and are secured within distal bearing assembly 20. The ends of struts 16 (only one is labeled) are coupled to distal bearing assembly 20 as shown, which may be disposed within and coupled to recessed regions of the distal bearing assembly 20. It should be understood that while the example above is described with respect to a distal impeller and the surrounding assembly, the same design can be used for a proximal impeller.

The catheter blood pump also includes an outer sleeve 40 coupled to distal bearing assembly 20 as shown, wherein outer sleeve 40 may have a varying stiffness along its length, which is described below with respect to the example in FIGS. 2A and 2B.

In this example the spring provides a variety of benefits and functions, but it is understood that in alternative blood pump assemblies, not all benefits and functions may be needed or even beneficial. It is thus understood that in alternative designs, the spring may provide more or fewer benefits than are described herein.

Force applier 30 generally applies an axial force to one or both of the distal bearing housing 20 and the drive cable extension 70. Spring 32 is coupled to the distal bearing assembly 20 (and in fact to housing 21 that is part of the distal bearing assembly 20) and to drive cable extension 70. During sheathing and collapse of the pump portion 10, the end of struts 16 apply a distal force to distal bearing assembly 20, and spring 32 compresses as distal bearing assembly 20 moves distally relative to drive assembly 60 (including drive cable 62). Any of the springs herein may be strong under tension but weak under compression. During unsheathing and pump portion expansion, distal bearing assembly 20 can move proximally relative to drive assembly 60. The spring force and spring length can be selected during manufacture so that the struts will assume a desired position when the pump is expanded, and will not be prevented from assuming a desired expanded configuration. For example, it is generally desired for the pump portion to assume a known expanded configuration, and the spring force and spring length may impact the configuration that the expandable pump portion assumes when it self-expands.

Spring 32 may be compressed and assembled into the blood pump in a compressed state, so that in use it applies a proximally directed force as described herein and optionally can also maintain tension in a drive cable in a central span between two impellers.

An exemplary benefit of spring 32 is that it provides distal support to the distal bearing assembly and prevents the distal bearing assembly from moving distally uncontrollably without limitation.

In some examples the spring is adapted, optionally by being compressed, to apply a proximally directed force on the housing to which it is coupled, which may then also apply a proximally directed force to struts 16 that are coupled to distal bearing assembly. This may help the pump assume and stay in its expanded configuration during pump operation, which may be critical for maintaining a gap between the distal impeller 14 and the surrounding blood conduit 12. In some examples the spring may be assembled in a compressed state, so that the spring always applies a proximally directed force on the distal bearing assembly during pump operation. In some merely exemplary embodiments, the spring may have a length from 0.1 to 1 inch, such as from 0.2 to 0.8 inches, and may be compressed to from 0.01 inches to 0.5 inches during assembly.

An additional consideration is that the spring force cannot be so great, however, that it prevents the blood conduit from collapsing during sheathing. The spring must therefore be able to compress to an extent that facilitates collapse of the pump, while still preferably applying a proximally directed force on the distal bearing assembly and the expandable pump via the struts.

An additional benefit of the spring is that by applying a proximally directed force on housing 21, the proximal force helps maintain contact between the surfaces of bearings 22 and 25 such that a gap doesn't exist. The spring force may also be selected so that the proximal force applied on the distal bearing assembly is not so great that excessive rubbing occurs as bearing 22 rotates relative to bearing 25.

An additional exemplary benefit of force applier 30 (e.g., spring 32) is that it can help maintain tension in the drive cable in the region between the impellers wherein there isn't an impeller shaft or impeller. For example, a compressed spring can apply a distally directed force on drive cable extension 70 or 700, which can help maintain tension in the drive cable. For example, it is generally undesirable for the drive cable to be compressed or have too much slack in that central span between the impellers, and the spring strength helps maintain tension in the drive cable 62 in that central span. Whipping can occur if there is too much slack in the drive cable in the central span between impellers.

During sheathing, distal bearing assembly 20 (including housing 21), all bearings 22-25, sleeve 40 which is coupled to distal bearing assembly 20, and tip 50 move together distally relative to drive assembly 60 (including drive cable 62) as spring 32 compresses.

Extension 70 may optionally be a metal material, and may be welded to one or both of the drive cable 62 and spring 32. Extension 70 provides a surface to which the distal end of the spring may be attached. Extension 70 also functions as a torque transmitter to impart torque to spring 32. In this example, extension 70 includes a distal end with an inner surface 71 that has a funnel configuration as shown in FIG. 1A, which can help front-load and guide a guidewire into the guidewire lumen defined by the inner surface of extension 70 and drive cable 62.

FIGS. 2A and 2B illustrate an exemplary blood pump 100 including a blood conduit 120 that is similar in many ways to the embodiment in FIGS. 1A-1D. The disclosure from any similarly labeled parts (e.g., 10 and 100, 14 and 140, 20 and 200, etc.) or similarly shown parts may be incorporated into the disclosure of FIGS. 2A and 2B unless specifically indicated to the contrary herein. One difference in FIGS. 2A and 2B is that the pump portion includes an optional thrust bearing 275 and housing 277 just distal to distal impeller 140. The thrust bearing housing 277 is coupled to the drive assembly 600 (e.g., including a drive cable and an impeller shaft thereon), and the thrust bearing rotates with the drive cable. Additionally, proximal thrust bearing 275 and housing 277 are not adapted to translate axially relative to the drive cable. As such, when distal bearing assembly 200 moves distally during collapse, a gap between thrust bearing 275 and bearing 240 and the rest of distal bearing assembly becomes greater. An additional consideration in this design is that the proximal force exerted by the spring should be great enough to also maintain contact between bearings 275 and 240, yet not too great to prevent sheathing and collapse of the pump portion. Similar to the embodiment in FIGS. 1A-1D, distal bearing assembly 200 (including housing 210), bearings 200, 240, 250 and 230" are adapted to move axially relative to the drive assembly 600.

As in the embodiment in FIGS. 1A-1D, the proximal end of the spring is adapted to move axially relative to the drive cable, but the distal end of the spring is not.

An additional difference that is not shown in FIGS. 1A-1D, but which may be incorporated therein, is that FIGS. 2A and 2B illustrate sleeve 400 with varying flexibility along its length. The sleeves herein in this context are coupled to the distal bearing housings and to the tips, which may have a curved configuration such as a J Tip (e.g., 50, 500). Some sleeves may be made of a material that is stiffer than the tips, and as such the transition between the sleeve and the tip can be susceptible to kinking. The sleeves herein may thus be adapted to include a varying flexibility, and may have a distal end that is more flexible than a proximal location to create a stiffness transition region so the change in stiffness is not as abrupt. In this example, sleeve 400 may be a hypotube, and may have one or more gaps 401 formed therein (e.g., laser cutting) in a distal region as shown in FIGS. 2A and 2B. The proximal end in this example is a solid section 402. Where the sleeve is coupled to an outer surface of a distal bearing assembly, as is shown, it may be helpful to have a solid tubular proximal region where it is coupled, and a more flexible distal region to impart the flexibility transition region, as shown. The sleeve 400 in FIGS. 2A and 2B can thus impart anti-kinking properties where the sleeve ends.

An additional benefit of having a more flexible distal end to the sleeve is to shorten the rigid length of the distal end of the pump, which is generally desirable to avoid damaging tissue.

In FIGS. 2A and 2B, the laser cut section has a proximal end in the region where spring 320 is disposed. An important consideration is that the flexibility of the sleeve must not be too great that the sleeve can bend and hit the rotating drive cable 62/620, spring 32/320, and extension 70/700. The flexibility of the sleeve is thus such that it can provide the variable stiffness region without contacting the rotating components therein. The sleeve may thus be considered to have a bending or flexibility limiter therein (e.g., which may include the laser cut pattern and features thereof) that prevents it from bending to and engaging the rotating components. As set forth above, the embodiment in FIGS. 1A-1D may also include sleeve 400.

Any of the suitable features shown or described with reference to FIGS. 1A-1D may be incorporated into the example in FIGS. 2A and 2B, and vice versa, even if those features are not described with respect to a particular embodiment.

As additionally described above, any of the embodiments herein which are described with respect to a distal portion of the pump or a distal impeller or distal impeller region can be applied to a proximal portion of the pump, such as a proximal impeller or proximal impeller region of the pump.

What is claimed is:

1. A catheter blood pump, comprising:
- a collapsible and expandable blood conduit having an inflow portion;
- proximal and distal impellers at least partially disposed in the blood conduit;
- a distal bearing assembly that is proximate the inflow portion;
- a rotatable drive assembly coupled to and extending through the proximal impeller, through the distal impeller, through the distal bearing assembly and extending distally beyond the distal bearing assembly;
- a plurality of distal struts coupled to the blood conduit and extending distally from the blood conduit at the inflow portion, the plurality of distal struts coupled to the distal bearing assembly; and
- a force applier secured to the distal bearing assembly and to a distal end of the rotatable drive assembly, and extending therebetween,
- wherein distal ends of the plurality of distal struts, the distal bearing assembly, and a proximal end of the force applier are axially movable relative to the rotatable drive assembly to facilitate collapse and expansion of the blood conduit.

2. The blood pump of claim 1, wherein the force applier is adapted to apply a proximally directed force on the distal bearing when the blood conduit is in an expanded configuration.

3. The blood pump of claim 2, wherein the proximally directed force is not large enough to prevent distal movement of the distal bearing assembly in response to sheathing forces, and thereby facilitates collapse of the blood conduit during sheathing.

4. The blood pump of claim 1, wherein the force applier comprises a compressed spring.

5. The blood pump of claim 1, further comprising a drive cable extension and a drive cable, wherein the force applier applies a distally directed force to the drive cable extension to thereby maintain tension in the drive cable in a region between the distal and proximal impeller to prevent whipping therein when the pump is operated.

6. The blood pump of claim 5, wherein maintaining tension prevents compression of the drive cable in the region between the impellers.

7. The blood pump of claim 1, further comprising at least two axially adjacent bearings disposed in the distal bearing assembly and wherein the force applier applies a compressive load to the distal bearing assembly sufficient to maintain axial contact between the at least two axially adjacent bearings.

8. The blood pump of claim 1, further comprising a drive cable and a bearing housing structure in the distal bearing assembly, wherein the force applier translates rotational force from a distal end of the drive cable to the bearing housing structure.

9. The blood pump of claim 1, further comprising a sleeve secured to the distal bearing assembly and disposed about the force applier, the sleeve extending further distally than the force applier.

10. The blood pump of claim 9, wherein the sleeve has a flexible distal end, and wherein the sleeve flexible end has a bend limiter that prevents the flexible end from contacting the force applier.

11. The blood pump of claim 10, wherein the bend limiter comprises a size of at least one gap formed through the sleeve.

12. The blood pump of claim 9, wherein the sleeve has a proximal end that is less flexible than a region distal to the proximal end.

13. The blood pump of claim 12, wherein the sleeve has a proximal end that is a solid tube.

14. The blood pump of claim 9, wherein the sleeve comprises a hypotube.

15. A catheter blood pump, comprising:
- a collapsible and expandable blood conduit;
- proximal and distal impellers at least partially disposed in the blood conduit;
- a distal bearing assembly that is proximate the inflow portion;
- a rotatable drive assembly coupled to and extending through the proximal impeller, through the distal impeller, through the distal bearing assembly and extending distally beyond the distal bearing assembly;
- a plurality of distal struts coupled to the blood conduit and extending distally from the blood conduit at the pump inflow, the plurality of distal struts coupled to the distal bearing assembly; and
- a sleeve coupled to the distal bearing assembly and extending about the rotatable drive assembly and distally thereof, the sleeve having a variable flexibility along its length with greater flexibility in a distal region than in a proximal region where it is coupled to the distal bearing assembly, wherein the variable flexibility is such that the sleeve at the distal region can bend but is prevented from contacting the rotatable drive assembly therein.

16. The blood pump of claim 15, wherein the rotatable drive assembly comprises a distal extension coupled to a distal end of a drive cable.

17. The blood pump of claim 15, further comprising a force applier secured to the distal bearing assembly and to a distal end of the rotatable drive assembly, and extending therebetween, wherein distal ends of the plurality of distal struts, the distal bearing assembly, and a proximal end of the force applier are axially movable relative to the rotatable drive assembly to facilitate collapse and expansion of the blood conduit.

18. A catheter blood pump, comprising:

a collapsible and expandable blood conduit;

proximal and distal impellers at least partially disposed in the blood conduit;

a distal bearing assembly that is proximate the inflow portion;

a rotatable drive assembly coupled to and extending through the proximal impeller, through the distal impeller, through the distal bearing assembly and extending distally beyond the distal bearing assembly;

a plurality of distal struts coupled to the blood conduit and extending distally from the blood conduit at the pump inflow, the plurality of distal struts coupled to the distal bearing assembly;

a force applier secured to the distal bearing assembly and to a distal end of the rotatable drive assembly, and extending therebetween; and wherein distal ends of the plurality of distal struts, the distal bearing assembly, and a proximal end of the force applier are axially movable relative to the rotatable drive assembly to facilitate collapse and expansion of the blood conduit, and wherein when the blood conduit is in an expanded configuration, a proximally directed force is being applied to a distal end of the distal bearing assembly.

19. The blood pump of claim 18, wherein the force applier applies the proximally directed load.

* * * * *